(12) United States Patent
Kolmakov et al.

(10) Patent No.: US 8,443,647 B1
(45) Date of Patent: May 21, 2013

(54) ANALYTE MULTI-SENSOR FOR THE DETECTION AND IDENTIFICATION OF ANALYTE AND A METHOD OF USING THE SAME

(75) Inventors: Andrei Kolmakov, Carbondale, IL (US); Victor V. Sysoev, Saratov (RU)

(73) Assignee: Southern Illinois University, Carbondale, IL (US)

( * ) Notice: Subject to any disclaimer, the term of this patent is extended or adjusted under 35 U.S.C. 154(b) by 517 days.

(21) Appl. No.: 12/576,940

(22) Filed: Oct. 9, 2009

Related U.S. Application Data

(60) Provisional application No. 61/103,982, filed on Oct. 9, 2008.

(51) Int. Cl.
| | | |
|---|---|---|
| *B82Y 15/00* | (2011.01) | |
| *B82B 1/00* | (2006.01) | |
| *G01N 27/04* | (2006.01) | |
| *G01R 27/22* | (2006.01) | |
| *G01R 35/00* | (2006.01) | |

(52) U.S. Cl.
USPC ............ 73/1.02; 73/1.06; 73/31.05; 324/601; 324/691; 324/703; 977/767; 977/810; 977/811; 977/832; 977/957

(58) Field of Classification Search
USPC .................. 73/1.02, 1.06, 19.1, 31.05–31.06, 73/53.01, 61.41, 61.61; 324/601, 691, 693, 324/703; 977/767, 810–811, 832, 953, 957
See application file for complete search history.

(56) References Cited

U.S. PATENT DOCUMENTS

| 5,783,154 | A | 7/1998 | Althainz et al. |
|---|---|---|---|
| 6,187,165 | B1 * | 2/2001 | Chien et al. .................... 205/118 |
| 7,531,136 | B2 * | 5/2009 | Besnard et al. ........... 73/31.06 X |
| 8,052,932 | B2 * | 11/2011 | Han et al. ................... 324/693 X |
| 8,159,235 | B2 * | 4/2012 | Lynch et al. ................... 324/691 |
| 2007/0240491 | A1 * | 10/2007 | Pavlovsky et al. ............ 73/31.05 |
| 2008/0078234 | A1 * | 4/2008 | Monty et al. ................. 73/31.05 |

(Continued)

FOREIGN PATENT DOCUMENTS

| EP | 1426756 A1 * | 6/2004 |
|---|---|---|
| WO | WO 0000808 A2 * | 1/2000 |

(Continued)

OTHER PUBLICATIONS

Brochure "DuPont TM Kapton® polymide film" Product Information section: Summary of Properties for DuPont TM Kapton® Polyimide Films [.pdf.], p. 2 at http://www2.dupont.com/Kapton/en_US/assets/downloads/pdf/summaryofprop.pdf, downloaded Mar. 19, 2012.*

(Continued)

*Primary Examiner* — Thomas P Noland
(74) *Attorney, Agent, or Firm* — Marshall, Gerstein & Borun LLP

(57) ABSTRACT

A multi-sensor as disclosed herein can include a substrate and at least three sensing elements disposed on the substrate. Each sensing element includes two electrodes separated by a distance and a nanowire mat adjacent to and in contact with the electrodes. The nanowire mats include nanowires which define a percolation network. The density of the nanowires in the nanowire mat of one sensing element is different than the density of the nanowires in the nanowire mat of either of the other at least two sensing elements.

22 Claims, 13 Drawing Sheets

U.S. PATENT DOCUMENTS

| | | | | |
|---|---|---|---|---|
| 2008/0094051 | A1* | 4/2008 | Williams et al. | 324/76.11 |
| 2008/0101994 | A1* | 5/2008 | Virji et al. | 422/94 |
| 2008/0157354 | A1* | 7/2008 | Zhang et al. | 977/953 X |
| 2008/0317636 | A1* | 12/2008 | Brahim et al. | 422/98 |
| 2009/0066348 | A1* | 3/2009 | Shin et al. | 324/693 |
| 2010/0001211 | A1* | 1/2010 | Huang et al. | 250/492.1 |
| 2010/0204062 | A1* | 8/2010 | Thompson et al. | 73/1.02 X |
| 2012/0036919 | A1* | 2/2012 | Kamins et al. | 73/31.05 |
| 2012/0108465 | A1* | 5/2012 | Duoss et al. | 506/12 |
| 2012/0112157 | A1* | 5/2012 | Quitoriano et al. | 977/957 X |
| 2012/0118751 | A1* | 5/2012 | Cai et al. | 977/832 X |
| 2012/0119760 | A1* | 5/2012 | Pehrsson et al. | 324/691 |
| 2012/0244537 | A1* | 9/2012 | Sun et al. | 435/6.11 |

FOREIGN PATENT DOCUMENTS

| | | | | |
|---|---|---|---|---|
| WO | WO 03008954 | A1 * | 1/2003 | |
| WO | WO 03078652 | A2 * | 9/2003 | |
| WO | WO 03093169 | A2 * | 11/2003 | |
| WO | WO 2005004204 | A2 * | 1/2005 | |
| WO | WO 2007001315 | A2 * | 1/2007 | |

OTHER PUBLICATIONS

Analyte—Wikipedia, the free encyclopedia, p. 1 of 1, last modified on Apr. 6, 2012, downloaded from http://en.wikipedia.org/wiki/Analyte.*

Analyte—definition of analyte in the Medical dictionary—by the Free Online Medical Dict . . . p. 1 of 1, Copyright © 2012 Farlex, Inc.Source URL: http://medical-dictionary.thefreedictionary.com/p/analyte, downloaded Oct. 10, 2012.*

Analyte—Definition and More from the Free Merriam-Webster Dictionary, p. 1 of 3, © 2012 Merriam-Webster, Incorporated, downloaded Oct. 10, 2012 from http://www.merriam-webster.com/dictionary/analyte.*

Analyte Definition—Definition of Analyte, p. 1 of 1, Education Chemistry, definition by Anne Marie Helmenstine, Ph.D., About.com, downloaded from http://chemistry.about.com/od/chemistryglossary/g/Analyte-Definition.htm on Oct. 10, 2012.*

Albert et al., "Cross-Reactive Chemical Sensor Arrays," Chem. Rev., 100:2595-2626 (2000), No. 7.

Arnold et al., "Field-Effect Transistors Based on Single Semiconducting Oxide Nanobelts," J. Phys. Chem. B, 107:659-663 (2003), No. 3.

Barsan et al., "Conduction Model of Metal Oxide Gas Sensors," J. Electroceram, 7:143-167 (2001).

Batzill et al., "The Surface and Materials Science of Tin Oxide," Prog. Surf. Sci., 79(2-4):47-154 (2005), scanned as two documents, pp. 47-100 & 101-154.

Buck et al., "A Novel Multigene Family May Encode Odorant Receptors: A Molecular Basis for Odor Recognition," Cell, 65(1):175-187 (1991), in April.

Comini, "Metal Oxide Nano-Crystals for Gas Sensing," Anal. Chem. Acta, 568:28-40 (2006).

Comini et al., "Stable and Highly Sensitive Gas Sensors Based on Semiconducting Oxide Nanobelts," Appl. Phys. Lett., 81:1869-1871 (2002), In September, No. 10.

Cui et al., "Nanowire Nanosensors for Highly Sensitive and Selective Detection of Biological and Chemical Species," Science, 293:1289-1292 (2001), in August.

D'Amico et al., "Portraits of Gasses and Liquids by Arrays of Nonspecific Chemical Sensors: Trends and Perspectives," Sens. Actuators, 68:324-330 (2000).

Dmitriev et al., "Nanoengineered Chemiresistors: The Interplay Between Electron Transport and Chemisorption Properties of Morphologically Encoded $SnO_2$ Nanowires," Nanotechnology, 18:055707 (2007), pp. 1-6.

Dolbec et al., "Sub-ppm Sensitivity Towards Carbon Monoxide by Means of Pulsed Laser, Deposited $SnO_2$: Pt Based Sensors," Appl. Phys. Lett., 90:173114 (2007), Pub. online in April, 3 pages.

Fan et al., "ZnO Nanowire Field-Effect Transistor and Oxygen Sensing Property," Appl. Phys. Lett., 85:5923-5925 (2004), in December, No. 24.

Freund et al., "A Chemically Diverse Conducting Polymer-Based Electronic Nose," Proc. Natl. Acad. Sci. U.S.A., 92:2652-2656 (1995), in March.

Goschnick, "An Electronic Nose for Intelligent Consumer Products Based on a Gas Analytical Gradient Microarray," Microelectron. Eng., 57-58:693-704 (2001).

Hagleitner et al., "Smart Single-Chip Gas Sensor Microsystem," Nature, 414:293-296 (2001), in November.

Hernandez-Ramirez et al., "High Response and Stability in CO and Humidity Measures Using a Single $SnO_2$ Nanowire," Sens., Actuators B, 121:3-17 (2007), Pub. online Oct. 2006.

Huang et al. "Catalytic Growth of Zinc Oxide Nanowires by Vapor Transport," Adv. Mater., 13:113-116 (2001), in January, No. 2.

Janata et al., "Chemical Sensors," Anal. Chem., 70:179R-208R (1998), in June, No. 12, scanned in as two documents, pp. 179R-193R & 194R-208R.

Jiang et al., "Ethylene Glycol-Mediated Synthesis of Metal Oxide Nanowires," J. Mater. Chem., 4:695-703 (2004).

Jurs et al., "Computational Methods for the Analysis of Chemical Sensor Array Data from Volatile Analytes," Chem. Rev., 100:2649-2678 (2000), No. 7.

Kalinin et al., "Electronic Transport Imaging in a Multiwire $SnO_2$ Chemical Field-Effect Transistor Device," J. Appl. Phys., 98:044503 (2005), 8 pages.

Kolmakov et al., "Detection of CO and $O_2$ Using Tin Oxide Nanowire Sensors," Adv. Mater., 15:997-1000 (2003), in June, No. 12.

Kolmakov et al., "Chemical Sensing and Catalysis by One-Dimensional Metal-Oxide Nanostructures," Annu. Rev. Mater. Res., 34:151-180 (2004), in March.

Kolmakov., "The Effect of Morphology and Surface Doping on Sensitization of Quasi-1D Metal Oxide Nanowire Gas Sensors," Proc. SPIE, 6370:63700X (2006), 8 pages.

Kong et al., "Nanotube Molecular Wires as Chemical Sensors," Science, 287:622-625 (2000), in January.

Kumar et al., "Percolating Conduction in Finite Nanotube Networks," Phys. Rev. Lett., 95:066802 (2005), in August, 4 pages.

Law et al., "Photochemical Sensing of $NO_2$ with $SnO_2$ Nanoribbon Nanosensors at Room Temperature," Angew Chem. Int. Ed., 41:2405-2408 (2002), No. 13.

Li et al., "$In_2O_3$ Nanowires as Chemical Sensors," Appl. Phys. Lett., 82:1613-1615 (2003), in March, No. 10.

Liang et al., "Catalytic Synthesis and Photoluminescence of $\beta$-$Ca_2O_3$ Nanowires," Appl. Phys. Lett., 78:3202-3204 (2001), in May, No. 21.

Lilach et al., "Encoding Morphology in Oxide Nanostructures During Their Growth," Nano Lett., 5:2019-2022 (2005), No. 10.

Lundström et al., "Artificial 'Olfactory' Images from a Chemical Sensor Using a Light-Pulse Technique," Nature, 352:47-50 (1991), in July.

Mitrovics et al., "Modular Sensor Systems for Gas Sensing and Odor Monitoring: The MOSES Concept," Acc. Chem. Res., 31:307-315 (1998), No. 5, pub. on Web May 1998.

Moroseac et al., "XPS and SSIMS Studies of Pd/$SnO_x$ System: Reduction and Oxidation in Hydrogen Containing Air," Surf. Sci., 566:1118-1123 (2004).

Pan et al., "Nanobelts of Semiconducting Oxides," Science, 291:1947-1949 (2001), in March.

Persaud et al., "Analysis of Discrimination Mechanisms in the Mammalian Olfactory System using a Model," Nature, 299:352-355 (1982), in September.

Ponzoni et al., "Ultrasensitive and Highly Selective Gas Sensors Using Three-Dimenonsional Tungsten Oxide Nanowire Networks," Appl. Phys. Lett., 88:203101 (2006), 3 pages.

Rothschild et al., "Gas Sensors: New Materials and Processing Approaches," J. Electroceram, 17:1005-1012 (2006).

Scofield, "Hartee-Slater Subshell Photoionization Cross-Sections at 1254 and 1487 eV," J. Electr. Spectr. Relat. Phenom., 8(2):129-137 (1976).

Shepherd, "Smell Images and the Flavour System in the Human Brain," Nature, 444:316-321 (2006), in November.

Sinner-Hettenbach et al., "Oxygen-Deficient $SnO_2$ (1 1 0): A STM, LEED and XPS Study," Surf. Sci., 477:50-58 (2001).

Sukharev., "Percolation Model of Adsorption-Induced Response of the Electrical Characteristics of Polycrystalline Semiconductor Adsorbents," *J. Chem. Soc., Faraday Trans.*, 559-572 (1993), vol. 89 (3).

Sysoev et al., "A Gradient Microarray Electronic Nose Based on Percolating SnO2 Nanowire Sensing Elements," *Nano Lett.*, 7(10):3182-3188 (2007), pub. on Web Oct. 10, 2007.

Sysoev et al., "Temperature Gradient Effect on Gas Discrimination Power of a Metal-Oxide Thin-Film Sensor Microarray," *Sensors*, 4:37-46 (2004).

Sysoev, "Toward the Nanoscopic 'Electronic Nose': Hydrogen vs Carbon Monoxide Discrimination with an Array of Individual Metal Oxide Nano- and Mesowire Sensors," *Nano Lett.*, 6: (2006), No. 8, pp. 1584-1588.

Wang et al., "Hydrogen-Selective Sensing at Room Temperature with ZnO Nanorods," *Appl. Phys. Lett.*, 86:243503 (2005), 3 pages.

Wang et al., "Synthesis and Characterization of Ultra-Fine Tin Oxide Fibers Using Electrospinning," *J. Am. Ceram. Soc.*, 88:2059-2063 (2005), in August, No. 8.

\* cited by examiner

ANALYTE MULTI-SENSOR FOR THE DETECTION AND IDENTIFICATION OF ANALYTE AND A METHOD OF USING THE SAME

FIELD OF THE INVENTION

The disclosure relates to a multi-sensor for the detection and identification of a gas in a sample, and more particularly, to a multi-sensor having a nanowire mat capable of detecting and identifying an analyte or irradiation in a sample.

BACKGROUND

A key requirement in the development of analytical sensor systems for industrial, medical, security, and domestic applications is their ability to promptly and reliably detect and recognize a broad range of analytes, often in low concentrations, while working in a continuous mode.

It is well-known that materials or chemical processes release characteristic complex gas ensembles that can be used like a fingerprint for condition monitoring. These complex gas ensembles are generally referred to as odors if perceptible by the human nose. Sensor systems are being designed to mimic the data acquisition principles of mammalian olfactory systems, which allow one to discriminate single gases as well as odor like gas ensembles by creating and processing a multidimensional pattern of many signals generated by a receptor (i.e. sensor) array. Devices employing this pattern recognition concept are generally referred to as electronic noses.

The KAMINA (Karlsruhe Research Center) platform is one example of a multielectrode nose. See U.S. Pat. No. 5,783,154. The key feature of the KAMINA technology is the substitution of an ensemble of separate conventional sensors with the gradient technique applied across the sensing elements. Conventional KAMINA technology applies the gradient to a single metal oxide layer deposited onto an array of Pt electrodes, with adjacent Pt electrodes forming a sensing element. Two gradients are typically applied across the sensor to differentiate the response of the sensing elements: (i) a lateral variation of surface temperature of the film; and (ii) a gradual thickness change of a gas permeable coating topping the metal oxide layer.

Recent developments in micro- and nanotechnologies have made available new material platforms, device fabrication alternatives, and novel sensing concepts to improve sensitivity, reliability, energy consumption, and response time of sensors. For example, quasi-one-dimensional metal oxide nanostructures have been found to be well suited for sensor applications because a multitude of sensing properties are substantially improved compared to compact metal oxide gas detecting elements. Namely, the high surface-to-bulk ratio of the quasi-one-dimensional metal oxide nanostructures allows very sensitive transduction of the gas/surface interactions (adsorption and catalytic oxidation) into a change of electrical conductivity. The radius of these nanostructures approaches the material's Debye length, which makes nearly the entire nanostructure a depletion or accumulation zone of mobile charge carriers in response to surface redox process, and thus establishes an extreme sensitivity of the electron or hole transport to charge transfer interactions of gas molecules at the surface. In addition, the nanostructures ability to accept a variety of morphologies and structures in conjunction with their surface and bulk doping offers wide possibilities to tune the gas-sensing properties. The contacts between the grains of conventional granular film sensing elements have propensity to sinter with time and therefore reduce stability of the sensor. Single crystal metal oxide nanowire mats have elevated resistance toward this phenomenon. Advantageously, the quasi-one-dimensional nanostructures render the empty space between adjacent nanostructures no matter how small the diameter of the individual nanowire, as compared to nanostructured oxide films, which hamper the gas diffusion with reduction of the grain size. There exists however a technological gap between the laboratory demonstrations using quasi-one-dimensional nanostructures as analyte sensors and a practical electron nose microdevice suitable for up to date, large scale microfabrication and capable of operating in real-world conditions environments.

SUMMARY OF THE INVENTION

In one embodiment of the disclosure, a multi-sensor for detection and identification of a target includes a substrate and at least three sensing elements disposed on the substrate. Each sensing element includes two electrodes separated by a distance, and a nanowire mat adjacent to and in contact with the electrodes. The nanowire mat includes nanowires defining a percolation network A density of the nanowires in the nanowire mat between the electrodes of one sensing element is different than a density of the nanowires in the nanowire mat between electrodes of either of the other at least two sensing elements.

In another embodiment of the disclosure, a method of detecting and identifying a target in a sample includes exposing a multi-sensor in accordance with the above-described embodiment to a sample comprising or suspected of comprising a target, detecting a change in resistance produced by each of the sensing elements in response to exposure to the sample, creating a response profile from the changes in resistance produced by the at least three sensing elements, and correlating at least a portion of the response profile to a known response profile to identify the target. The presence of the detectable responses corresponds to the presence of the target in the sample and the absence of a detectable response corresponds to the absence of the target in the sample.

In yet another embodiment of the disclosure, a method of calibrating the multi-sensor in accordance with the above-described embodiment include exposing the multi-sensor to a known analyte or irradiation, detecting a change in resistance produced by each sensing element in response to the known analyte or irradiation; and creating a response profile from the changes in resistance produced by the at least three sensing elements.

The above and other aspects and advantages will become apparent from the following detailed description taken in conjunction with the drawings.

BRIEF DESCRIPTION OF THE DRAWINGS

FIG. 7a is a schematic representation of a method of forming the nanowire mats;

FIG. 7b is a scanning electron microscopy image of the nanowire mats formed in accordance with the method of FIG. 7a;

FIG. 7c is a graph showing the change of temperature as a function of time during the formation method of FIG. 7a;

FIG. 8a is an X-ray diffraction pattern (log scale) of the nanowire mat of the multi-sensor of FIG. 1a;

FIG. 8b is an X-ray photoelectron spectroscopy image of the nanowire mat of the multi-sensor of FIG. 1a, showing the structural homogeneity and surface purity of the nanowire mat;

FIG. 11a is schematic representations of the experimental setup used to measure a gas response of a multi-sensor in accordance with an embodiment of the disclosure when exposed to a target gas;

FIG. 11b is a schematic representation of the gas-mixing step of the experimental setup of FIG. 10a;

FIG. 11c is a photograph showing three KAMINA units equipped with sensors in accordance with an embodiment of the disclosure and being fed by a gas flow.

DETAILED DESCRIPTION

The invention may be understood more readily by reference to the following detailed description of the invention and the examples provided therein. It is to be understood that this invention is not limited to the specific components, articles, processes and/or conditions described, as these may, of course, vary. It is also to be understood that the terminology used herein is for the purpose of describing particular embodiments only and is not intended to be limiting.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Disclosed herein is a sensor (also referred to herein as a multi-sensor) for the detection and identification of an analyte or an irradiation in a sample, and a method of using the same to detect and identify a target analyte or irradiation in a sample containing or suspected of containing the target. The multi-sensor is capable of producing a detectable response when exposed to the target. The specificity of the detectable response to individual targets can allow for identification of the target in addition to detecting the presence or absence of the target in the sample. For example, the detectable responses can be used to create a response profile, at least a portion which can be correlated to known response profiles to identify the target.

Multi-Sensor

Figure 1:
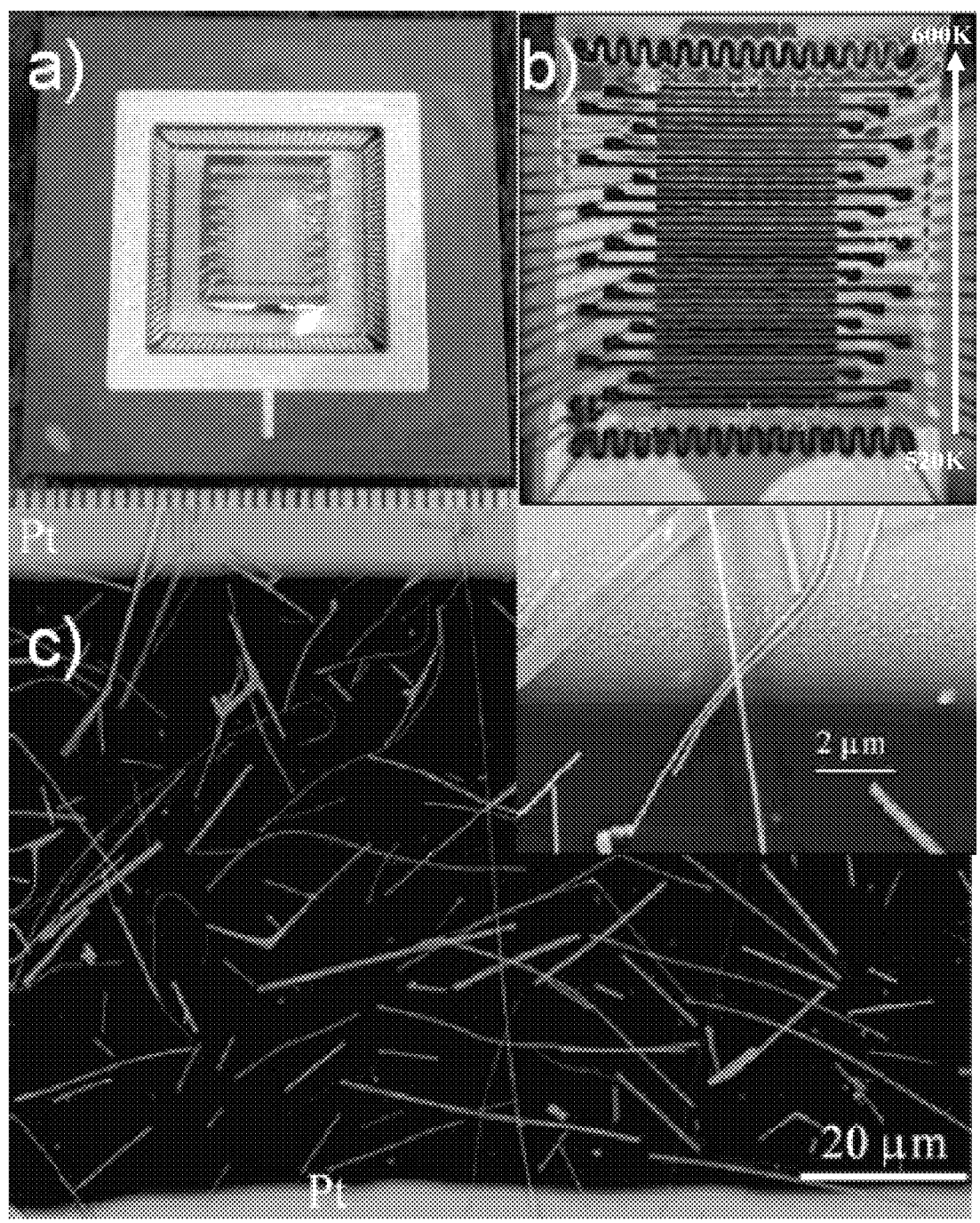
FIG. 1a is a photograph showing a multi-sensor in accordance with an embodiment of the disclosure having a $SnO_2$ nanowire mat formed over a KAMINA substrate.
FIG. 1b is an infrared image of the multi-sensor of FIG. 1a under application of a temperature gradient, wherein the temperature ranges from about 520K to about 600 K.
FIG. 1c is a scanning electron microscopy image of a sensing element of the multi-sensor of FIG. 1a, showing the $SnO_2$ nanowires disposed between two Pt coplanar electrodes.

Referring to FIG. 1, the multi-sensor includes a substrate and at least three sensing elements formed on the substrate. The sensing elements each include two electrodes separated by a distance, and a nanowire mat disposed adjacent to and in contact with the electrodes. For example, individual nanowires mats can be provided adjacent to and in contact with the electrodes of the sensing element. Alternatively, a single nanowire mat can be provided across the multi-sensor or a portion of the multi-sensor such that portions of the nanowire mat are adjacent to and in contact with the electrodes of the sensing elements. For ease of reference the nanowire mat of the sensing element should be understood to include either arrangement or a combination thereof (i.e. each sensing element having individual nanowire mats or each sensing element having a portion of a nanowire mat disposed across the multi-sensor). Each gas sensing element is capable of producing a detectable response in response to being exposed to an analyte or an irradiation, for example, a gas or an irradiation. The nanowire mat (or nanowire mat portion) of one sensing element includes a different density of nanowires than the nanowire mat (or nanowire mat portion) of either than the other at least two sensing elements. The different nanowire densities of the nanowire mats of sensing elements can form a density gradient across the multi-sensor. Alternatively, the different nanowire densities of the nanowire mats of the sensing elements can vary randomly across the multi-sensor. Preferably, the density of the nanowire mat is measured as the number of nanowires per unit area in the nanowire mat. The multi-sensor can be incorporated into conventional electronic nose platforms, such as, for example, the KAMINA platform.

The multi-sensor can include any non-conducting substrate. For example, the substrate can be a $SiO_2/Si$ substrate, an $Al_2O_3$ substrate, a $Si_3N_4$ substrate, a Kapton film, a glass substrate, a sapphire substrate, a quartz substrate, and combinations thereof. The substrate can be sized so that the multi-sensor fits in a conventional electronic nose platform, such as for example the KAMINA's standard chip housing. For example, the chip can be 4×8 $mm^2$. The substrate can further include one or more heaters that can provide a temperature gradient across the substrate. The heaters are preferably disposed on the side of the substrate opposite the sensing elements. The heaters can be, for example, meander-shaped platinum heaters. The heaters can have, for example, any convoluted shape, for example, tortuous, serpentine, winding, or boustrophedonic.

The multi-sensor includes at least three sensing elements. The number of sensing elements is limited only by the ability of the corresponding electronics unit to read out all the sensing element responses in a real time scale, and the resolution of the microelectronic technology applied to fabricate the electrodes. The electrode can be arranged, for example, substantially parallel to one another on the substrate. The electrodes can also be arranged as outer and inner electrodes as described in U.S. Pat. No. 5,783,154, the relevant disclosure of which is incorporated herein by reference.

The number of electrodes is dependent upon the number of sensing elements in the multi-sensor. The multi-sensor includes at least one more electrode than sensing element. For example, a multi-sensor that includes 38 sensing elements would include 39 electrodes. The multi-sensor includes at least 4 electrodes. Adjacent electrodes, separated by a distance, form the two electrodes of the sensing elements. The electrodes can be apart of two sensing elements.

The electrodes can be formed from any metal or metal alloy. For example, the electrodes can be formed from platinum, gold, chromium, Ni, ITO, and combinations thereof. The electrodes can be about 0.01 µm to about 10 µm thick, For example, the electrodes can have a minimum thickness of about 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 µm. For example, the electrodes can have a maximum thickness of about 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 µm. Specific electrode thicknesses include, but are not limited to, about 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, and 10.0 µm. The electrodes can be fabricated by any known method. For example, the electrodes can be fabricated using electron or photo-lithography, by rf magnetron sputtering, Dip Pen Lithography, Nanoimprint lithography, electron beam, laser or thermal evaporation through a shadow mask.

The distance separating the electrodes in a sensing element can be, for example, in a range of about 0.1 µm to about 200 µm. For example, the minimum distance can be about 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 175, 180, 185, 190, 195, or 200 µm. For example, the maximum distance can be about 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 175, 180, 185, 190, 195, or 200 µm. Specific examples of distances include, but are not limited to, about 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 175, 180, 185, 190, 195, and 200 µm. The distance between electrodes can be substantially equal for each sensing element, or the distance can vary among different sensing elements.

The nanowire mat is formed from a percolation network of nanowires. A percolation network forms through overlapping nanowires, such that a percolation path is defined by the straight nanowires and the contact points formed between overlapping nanowires. The contact points between nanowires are referred to herein as "nodes." The number of nodes in a nanowire mat can be adjusted by changing the density of nanowires in the nanowire mat. Preferably, the density of the nanowires in the nanowire mat is measured as the number of nanowires per unit area. The nanowires can be woven, for example, into the nanowire mat. When multiple layers of nanowire mats are used, the percolation network forms among the layers and can interconnect the layers. The nanowire mat is preferably structurally and chemically homogeneous. Preferably, the nanowires have a length less than the distance between the electrodes so as to form the percolation network. Some of the nanowires, however, can be long enough to bridge the distance between the electrodes.

A used herein, "nanowire" refers to nanostructures including, for example, nanowires, nanotubes, nanobelts, whiskers, nanobeams, nanofibers, nanorods, segmented nanorods, and nanoribbons. The diameters of the nanowires can be, for example, in a range of about 20 nm to about 500 nm. For example, the nanowires can have a minimum diameter of about 20, 25, 30, 35, 40, 45, 50, 55, 60, 65, 75, 80, 85, 90, 95, 100, 105, 110, 115, 120, 125, 130, 135, 140, 145, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nm. For example, the nanowires can have a maximum diameter of about 20, 25, 30, 35, 40, 45, 50, 55, 60, 65, 75, 80, 85, 90, 95, 100, 105, 110, 115, 120, 125, 130, 135, 140, 145, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nm. Specific examples of nanowire diameters include, but are not limited to, about 20, 25, 30, 35, 40, 45, 50, 55, 60, 65, 75, 80, 85, 90, 95, 100, 105, 110, 115, 120, 125, 130, 135, 140, 145, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 nm. The nanowire lengths can be, for example, in a range of about 1 µm to about 1000 µm. For example, the nanowires can have a minimum length of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 µm. For example, the nanowires can have a maximum length of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 µm. Specific examples of nanowire lengths include, but are not limited to, about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 µm.

The nanowires are preferably metal oxide nanowires. For example, the nanowires can be $SnO_2$ nanowires, $WO_3$ nanowires, $In_2O_3$ nanowires, $TiO_2$ nanowires, ZnO nanowires, NiO nanowires, CuO nanowires, $V_2O_5$ nanowires, $Ga_2O_3$ nanowires, and combinations thereof. The nanowires can further include surface functionalization, such as for example, by noble metals and foreign oxides (i.e. oxides different that the oxide used to form the nanowire). The surface functionalization can be spatially varied across the multi-sensor elements so as to define a surface functionalization gradient across the multi-sensor.

The nanowire mats can be formed according to known methods. See Sysoev, Nano Lett. 6, 1548 (2006), the disclosure of which is incorporated herein by reference. For example, $SnO_2$ nanowires can be grown on alumina plates at 1280K under 200 Torr of Ar carrier gas. The nanowires can then be dry-pressed mechanically onto the substrate. The density of nanowires can be increased by forming multiple nanowire mats over the substrate so as to form layers of nanowire mats. Without intending to be bound by theory, it is believed that the adhesion of the nanowires to the substrate is due to the electrostatic affinity of the substrate surface. It is preferred that no wet processes, such as those used in resist-based lithography, are used at any stage of multi-sensor formation to prevent contamination of the nanowire mat surface.

Figure 2:
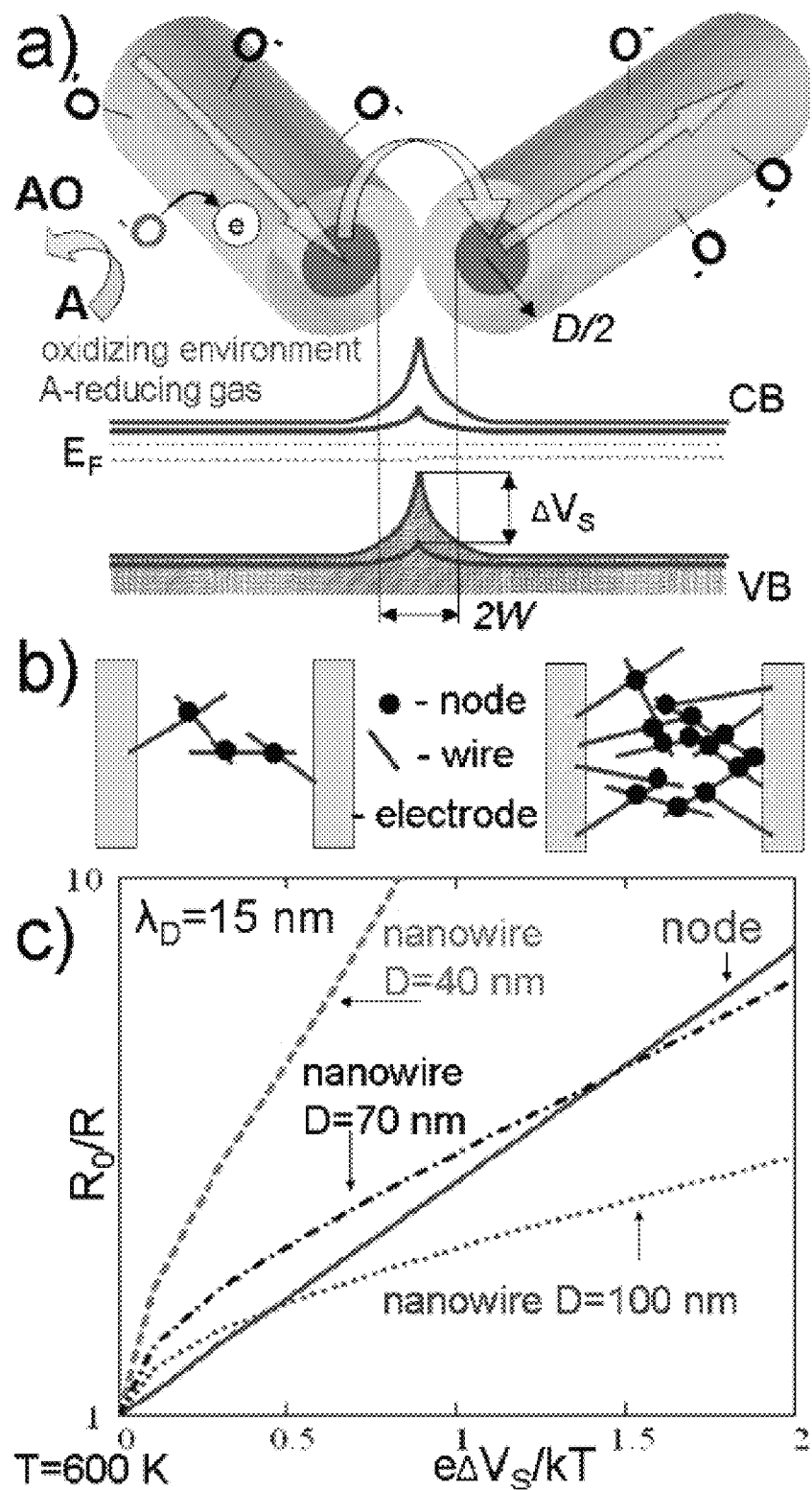
FIG. 2a is a schematic showing the receptor and transduction functions of the percolating nanowire mat, wherein in an oxidizing ambient, the exposure to reducing gas leads to a decrease in the contact barriers and an increase of the cross-section of the conducting channels inside the nanowires.
FIG. 2b is a schematic showing that an increase in nanowire density leads to an increase of the relative contribution of nodes with respect to straight nanowires to the percolating path.
FIG. 2c is graph (log scale) showing the relative contribution of nodes and nanowires to the detectable response.

The multi-sensor is capable of detecting and identifying targets such as analytes, such as gases, and irradiation. When the target analyte is a gas, without intending to be bound by theory, it is believed that the morphology of the nanowire mat enhances the response transduction mechanism of the multi-sensor. Referring to FIG. 2, the current transport through the nanowire mat has a percolating character, where the conductance between two adjacent electrodes is determined by the availability of conduction paths through the nanowire mat. Without intending to be bound by theory, it is believed that at least two mechanisms contribute concomitantly in the transduction function of the multi-sensor. First, adsorbate-induced change of the potential barrier heights $\Delta V_S$ at the nodes effectively modulates the transport properties between two overlapping nanowires. The current has to pass at the overlapping wires through the charge carrier depletion zones of both wires. The electron transport in the node area can be described in terms of a thermoelectronic emission mechanism. Thus, the multi-sensor detectable response due to adsorbate-induced alternating barrier on the node is:

$$\left[\frac{R_0}{R}\right]_{NODE} \approx \exp\left(\frac{e\Delta V_S}{kT}\right)$$

where $R_0$ and R are the multi-sensor segment's resistance in air and upon admission of an electron-spending gas, correspondingly; T is the operating temperature; e is the elementary charge; and k is Boltzmann's constant.

The second mechanism is the adsorbate influence on the electron transport inside the straight nanowire. The semiconducting core of the nanowire is surrounded by an electron depletion region with a width W. The depletion width is dependent on the Debye length $\lambda_D$ of the nanowire and the steady-state coverage of the ionosorbed acceptor molecules ($O_2$, $O^-$, and $OH^-$) from the ambient air at the operating temperature. The depletion width W will vary due to the reaction with the reducing gas, thus widening the cross section of the conducting channel. The straight nanowire contribution to the detectable response is approximately:

$$\left[\frac{R_0}{R}\right]_{wire} = \left(\frac{D}{D-2\Delta W}\right)^2 = D^2\left(D - 2\lambda_D\left(\frac{e\Delta V_S}{kT}\right)^{1/2}\right)^{-2}$$

where $R_0$ and R are the multi-sensor segment's resistance in air and upon admission of an electron-spending gas, correspondingly; T is the operating temperature; W is the depletion width; D is the diameter of the nanowire; e is the elementary charge; k is Boltzmann's constant; and $\lambda_D$ is the Debye length of the nanowire.

As shown in FIG. 4c, the relative contributions of the nodes and the straight nanowires to the chemiresistive response are comparable for nanowires having a length capable of bridging the distance between adjacent electrodes. The nanowire mat, however, contains a plurality and preferably a majority of nanowires that are shorter than the distance between the adjacent electrodes. Referring to FIG. 2b, the shorter the nanowires and the higher the density of nanowires, the more nodes the current has to pass through and the shorter the average travel length between the two nodes. It is preferred that the density of the nanowire mat is stochastically different from sensing element to sensing element. The varied density can result from the deposition method used. Alternatively, the density of nanowires in the nanowire mat can be controlled to form a density gradient across the multi-sensor. The varying density of nanowires changes the ratio of nodes to straight nanowires for each sensing element. For example, an increase in density of the nanowires can increase the nodes' contribution to the response of the sensing element. This provides specificity of the response to an analyte or an irradiation for any individual sensing element. Thus, the sensitivity and discrimination power a multi-sensor can be tuned by varying the density and length of the nanowires in the nanowire mat.

Figure 3:
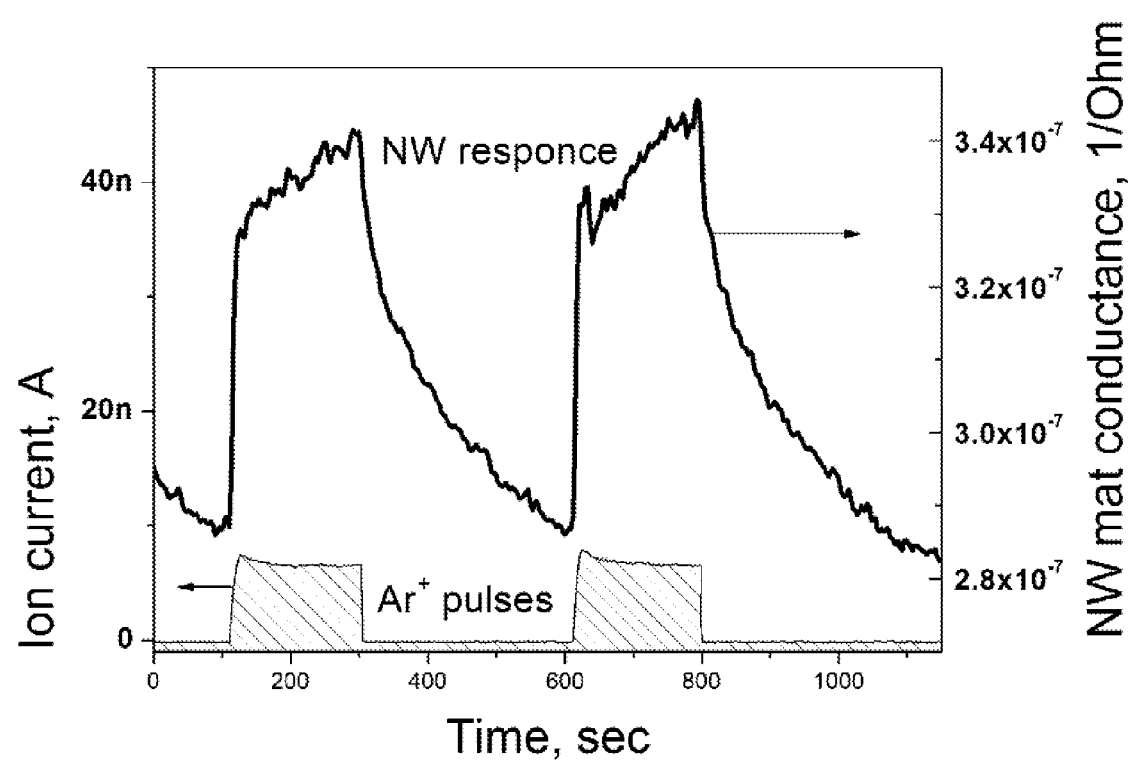
FIG. 3 is a graph showing the detectable response of a multi-sensor in accordance with an embodiment of the disclosure when exposed to Ar ions.

The multi-sensors are also capable of detecting and identifying irradiation, such as, for example, UV radiation, thermal radiation, charged particles, and radioactivity. Without intending to be bound by theory, it is believed that the receptor principle of the multi-sensor towards these irradiation agents is based on generation of electron-hole pairs inside the nanowire mats. The efficiency and specificity of the detectable responses to exposure of the irradiation agents results from the characteristics of the radiation and parameters of the nanowire mats. The transduction principle is based on the radiation induced reduction/increase of the conducting channel in the depleted nanowires (for slow ions, such as UV radiation) or energy/projectile type dependent increase of the concentration of electron-hole pairs in the nanowire mats. FIG. 3 demonstrates the multi-sensors response to exposure to Ar ions.

Detection and Identification of a Target

The multi-sensor can be used in target analyte and/or target irradiation detection and identification schemes. As used herein, the term "target" refers to an analyte or irradiation of interest, which is detectable and identifiable by the multi-sensor. The target can be, for example, a single gas, one or more gases in a mixture, and/or irradiations. Irradiations agents can include, for example, ultraviolet radiation, thermal radiation, charged particles, and radioactivity. The multi-sensor is exposed to a sample having or suspected of having a target. The sensing elements each produce detectable responses, for example, changes in resistance, in response to exposure to the target. The change in resistance can be detected directly or indirectly, for example, by the change in current or voltage. The detectable responses are then detected.

Figure 4:
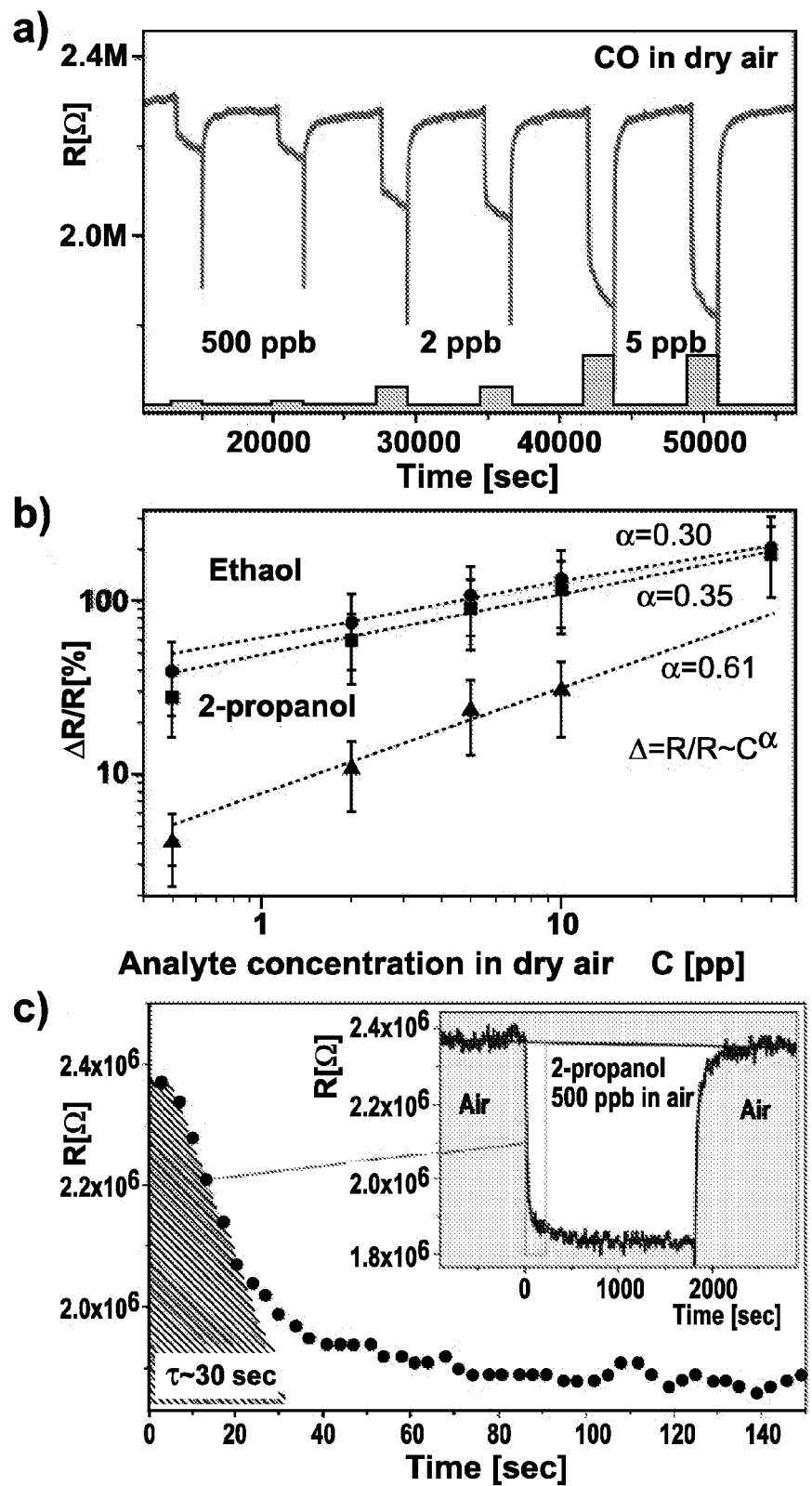
FIG. 4a is a graph showing the median sensing element resistances for the multi-sensor of FIG. 1a during exposure to a sequence of CO pulses (500 ppb, 2 ppm, and 5 ppm)
FIG. 4b is a graph showing the average relative resistance change of the sensing elements of the multi-sensor of FIG. 1a as a function of the concentration of three test gases (ethanol, 2-propanol, and ethanol)
FIG. 4c is a graph showing the temporal evolution of the resistance of the middle sensing elements of the multi-sensor of FIG. 1a upon exposure to 500 ppb of 2-propanol in air; wherein the time constant is defined as the intersection of the initial slope of the response with its saturated value.
Figure 5:
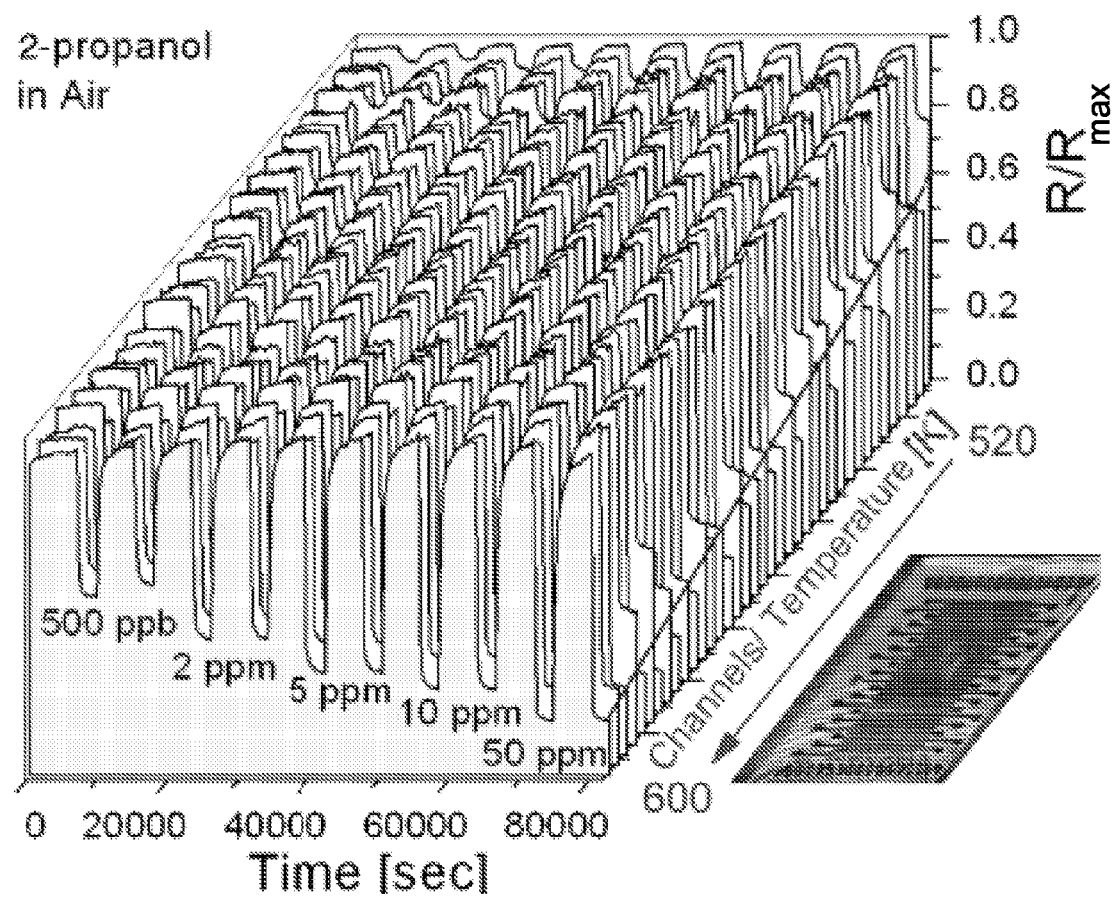
FIG. 5 is a graph showing the normalized resistance response of the 38 sensing elements of the multi-sensor of FIG. 1a upon exposure to 2-propanol pulses when an 80 K thermal variation is established across the multi-sensor, wherein the side line indicates the growth of the responsiveness with the temperature.

The presence or absence of the detectable responses corresponds to the presence or absence of the target in the sample. Furthermore, if detectable responses are produced, the specificity of the sensing elements responses to particular analytes and/or irradiations can be used to identify the target as a specific gas or a specific irradiation type. For example, the detectable responses can be used to create a response profile. The target can then be identified by correlating the response profile to known response profiles. The known response profiles can be determined by calibrating the multi-sensor to known analytes and/or irradiations. For example, the multi-sensor can be calibrated by exposing the multi-sensor to a known analyte, detecting the detectable response, and creating the known response profile. The known profiles can then be correlated during target detection to identify the target. Referring to FIGS. 4 and 5, for example, the multi-sensor can be exposed to a sample containing 2-propanol. The sensing elements produce detectable responses in response to the exposure to the 2-propanol. As a result of the specificity of the multi-sensor responses to a particular analyte, the sensing element responses can be used to identify the analyte as 2-propanol. For example, a response profile can be created from the detectable responses and correlated to the known response profile for 2-propanol to identify the analyte in the sample as 2-propanol. The identity of the target can be readily determined by the response profile created from the detectable responses.

Figure 6:
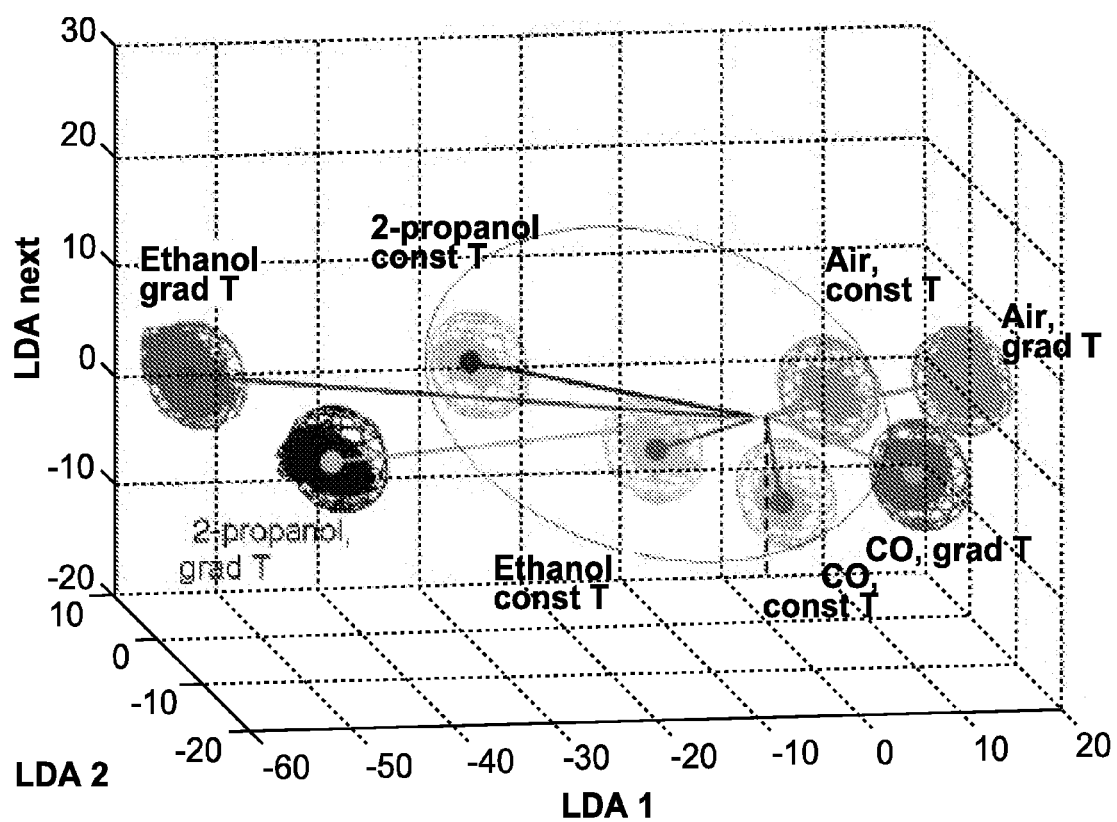
FIG. 6 is a graph showing an linear discriminant analysis of the detectable responses obtained upon exposure of the multi-sensor of FIG. 1a to test gases in a concentration range of 2 ppm to 10 ppm under (a) quasihomogenous heating at 580 K and (b) a temperature gradient of 520 K to 600 K, wherein the classification spheres correspond to a normal distribution of data at a 0.9999 confidence level.
Figure 12:
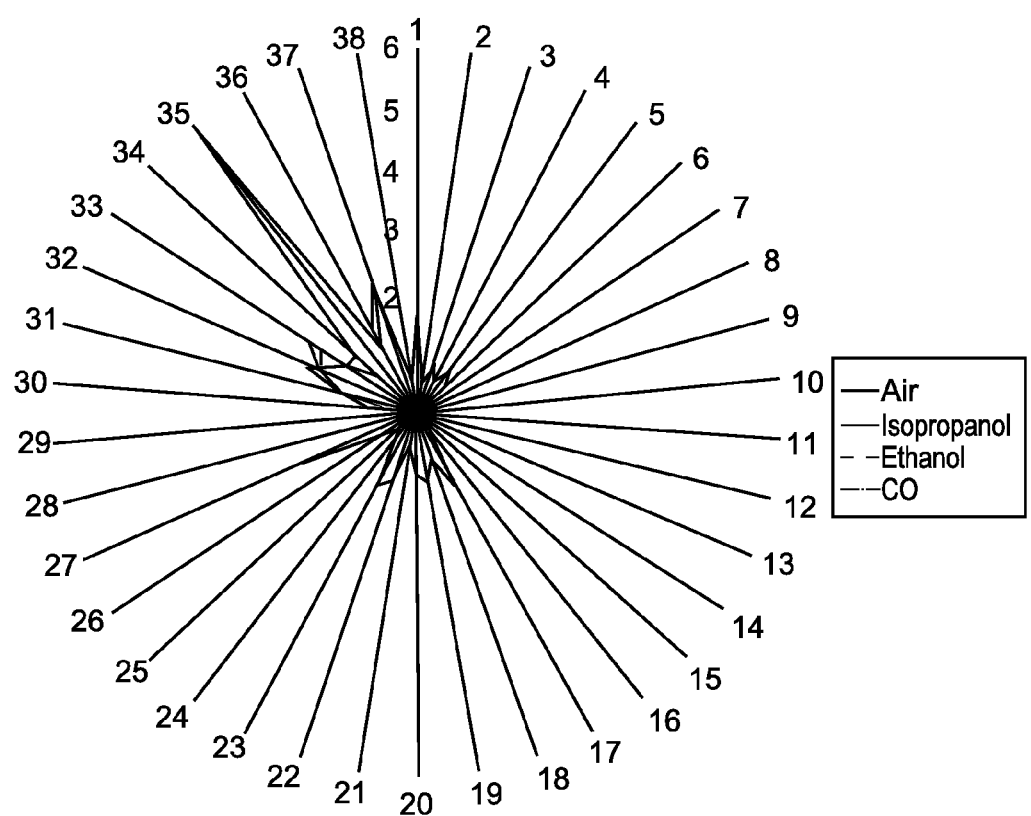
FIG. 12 is a graph showing the distribution of sensing element resistances over a multi-sensor in accordance with an embodiment of the disclosure when exposed to 5 ppm of a target gas mixture and air.

The multi-sensors can be used to detect and identify a mixture of targets in a sample containing or suspected of containing the mixture of targets. The multi-sensor is exposed to the sample and produces a detectable response to the particular targets. The response is then detected to determine the presence or absence of the targets as well as identify the specific targets in the mixture. The targets can be individually identified by the multi-sensor. For example, the sensor elements produce distinct detectable responses for each of the targets in the mixture. Distinct response profiles can be created from the distinct detectable responses. Each of the response profiles can then be correlated to known profiles to identify each of the targets in the mixture. Referring to FIGS. 4b, 6, and 12, for example, a multi-sensor can be exposed to a gas mixture containing, for example, air, CO, 2-propanol, and ethanol. The sensing elements can produce detectable responses distinct to the individual gases, such that the components of the gas mixture (air, CO, 2-propanol, and ethanol) can be identified.

The method of detecting and identifying a target can further include applying a gradient across the multi-sensor to differentiate the properties of the sensing elements. For example, a temperature gradient can be applied across the multi-sensor. A gradient of the density of the nanowires in the nanowire mat can also be applied. Other gradients include nanowire thickness and surface functionalization.

Linear Discriminant Analysis

Response profiles can be created from the detectable responses from the at least three sensing elements using, for example, Linear Discriminant Analysis (LDA). Referring to FIG. 6, LDA can be performed to interpret and characterize the detectable response data produced by the sensing elements when exposed to a target. Other known pattern recognition methods for characterizing the detectable responses and creating a response profile from the detectable responses can also be used. For example, principal component analysis, regression analysis, cluster analysis, linear discriminant analysis, and combinations thereof can be used to create a profile from the detectable responses. The pattern recognitions methods can also be used to correlate the response profile to known response profiles to identify the target.

LDA is based on presentation of the multi-sensor detectable responses as ensembles of points in N-dimensional space, where N is the number of sensing elements in the multi-sensor. The detectable responses are classified into classes and matched to known analyte or irradiation data by LDA as a search of the coordinate system. This maximizes the scatter of detectable response data related to different classes and minimizes the scatter of data related to a single class. Classification and identification are solved by LDA under the following assumptions:

The relationship between the space of array responses and the LDA space is linear.

The data within a single class are scattered according to the normal distribution.

The probability distribution of variables is the same for all classes.

A squared Mahalanobis distance of centers of classes is used as the criteria for class recognition.

The following matrices $\hat{T}, \hat{B}, \hat{W}$ are used to characterize the common scatter of calibration data (i.e. known response profiles), the scatter between classes, and the scatter of data inside a single class, respectively.

$$t_{iu} = \sum_{k=1}^{n} (X_{ki} - \overline{X}_i)(X_{kj} - \overline{X}_j);$$

$$b_{ij} = \sum_{l=1}^{g} n_l (X_i^l - \overline{X}_i)(\overline{X}_j^l - \overline{X})_j;$$

$$w_{ij} = \sum_{l=1}^{g} \sum_{k \in S_l} (X_{ki} - \overline{X}_i^l)(X_{kj} - \overline{X}_j^l);$$

where g is the number of classes (i.e. the number of test gases); n is the number of data points; k is the index of points; l indexes the classes; $n_l$ is the number of points inside the class $S_l$; $\overline{X}_i$, is the average coordinate value taken over all the data; and $\overline{X}_i^l$ is the average coordinate value taken over the data related to a single class. The coordinate system is searched to find the linear independent vectors $\overline{u}$ which give $$\frac{\overline{u}' \hat{B} \overline{u}}{\overline{u}' \hat{W} \overline{u}}$$

a maximum value. This is done by solving the equation for eigenvectors and eigen values $\hat{T}^{-1} \hat{B} \overline{u} = \lambda \overline{u}$. The number of obtained vectors is equal to g–1.

Additional aspects and details of the invention will be apparent from the following examples, which are intended to be illustrative rather than limiting.

EXAMPLES

Formation of Tin Oxide Nanowire Mats

Figure 7:
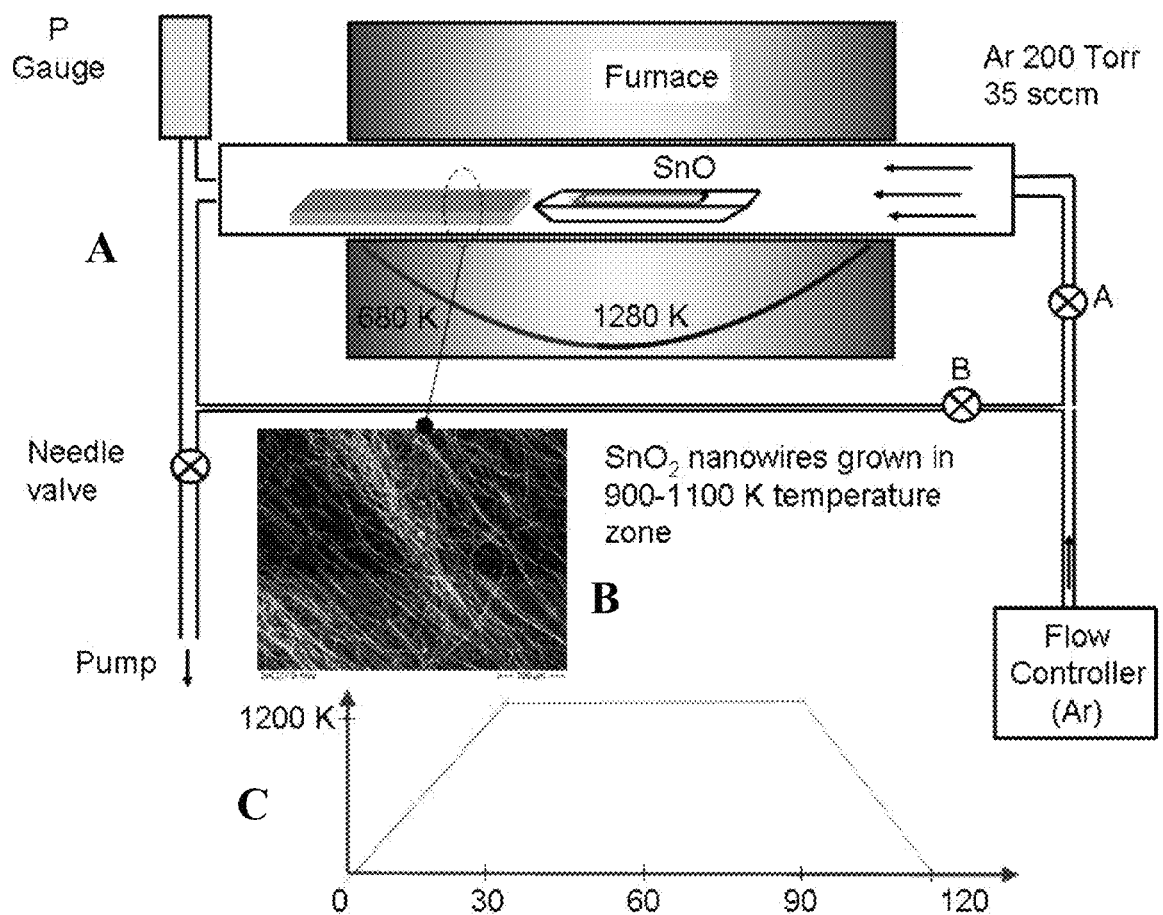

Referring to FIG. 7, $SnO_2$ nanowire mats were grown using vapor methods (VS) in a quartz tube furnace. SnO (Sigma-Aldrich, 99.99%) was used as a source material and placed in the center of the furnace. The operating temperature was maintained at about 1280 K. The tube was initially pumped to ca $10^{-2}$ Torr and further fed with constant Ar (99.995%) flux of 30 sscm rate. The pressure inside the tube was kept at 200 Torr using a needle valve. $SnO_2$ rutile nanowires with the highest densities and length of about a few hundred microns were generally observed in the tube zone where the temperature was in a range of 900 K to 1100 K. The as-synthesized nanowires were then collected and mechanically dry pressed over the surface of a $SiO_2/Si$ KAMINA substrate with 39 pre-deposited Pt electrodes to avoid potential contamination from the lithography protocols. The resultant layer demonstrated excellent adhesion and sufficient thermo-mechanical stability.

Figure 8:
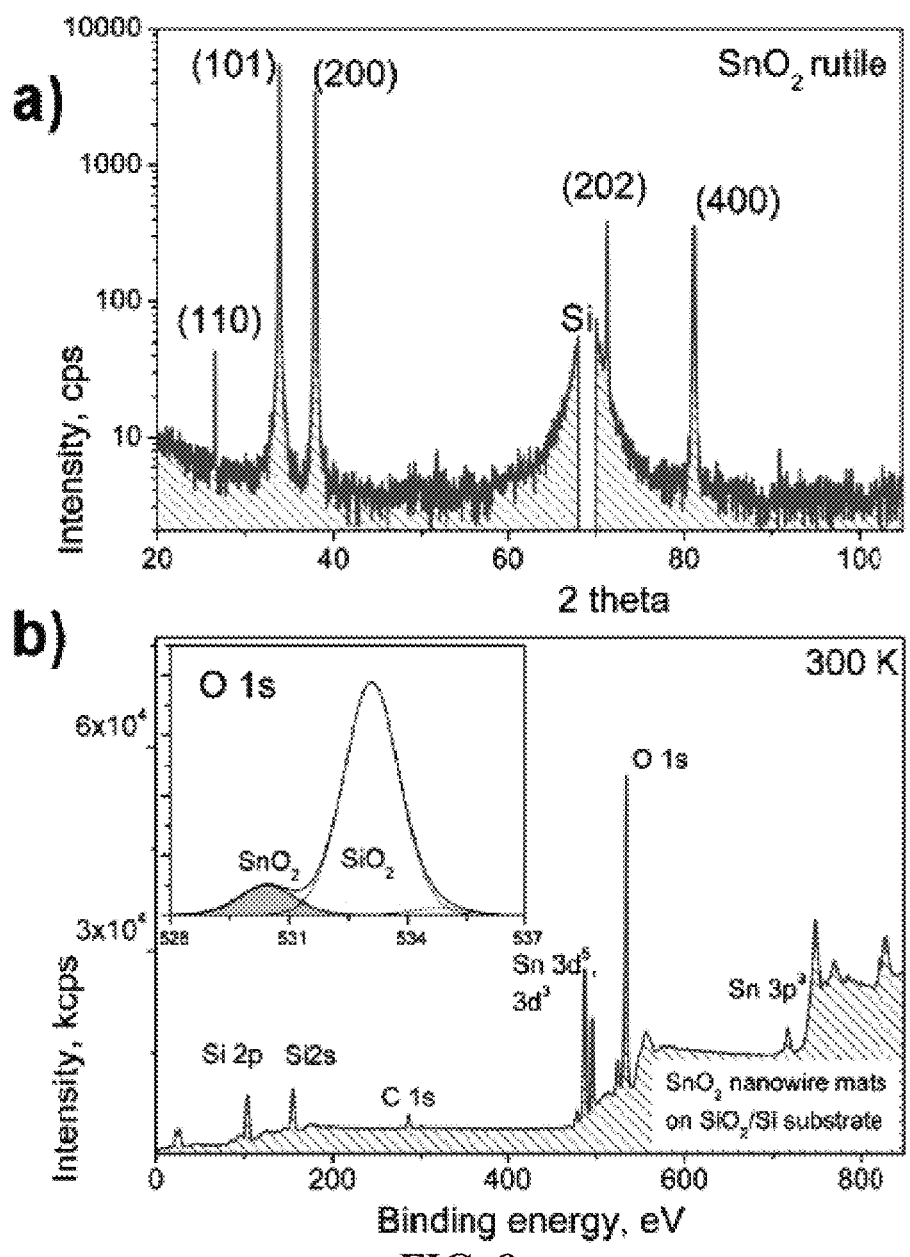
Figure 9:
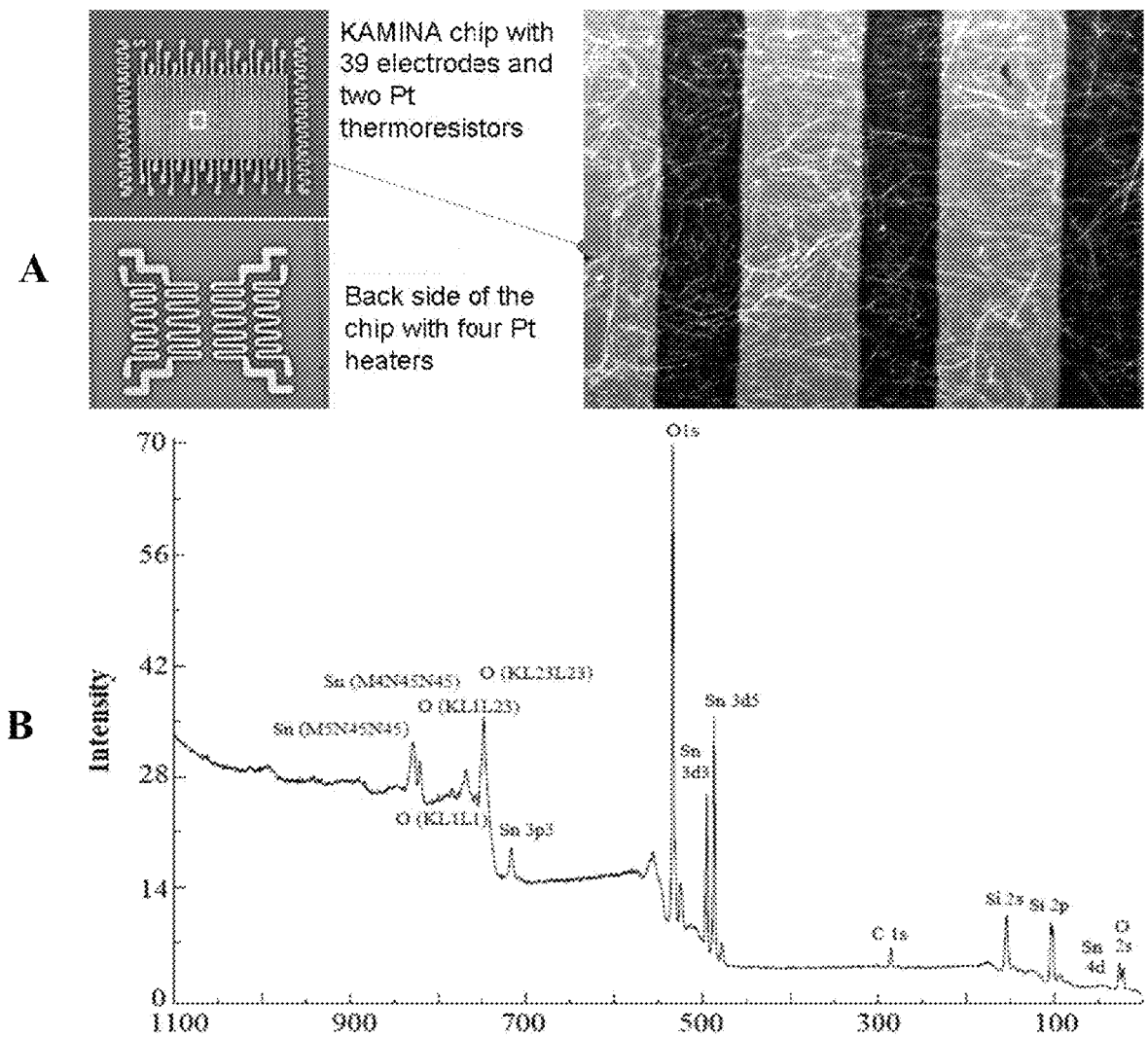
FIG. 9a is a scanning electron microscopy image of a portion of a multi-sensor in accordance with an embodiment of the disclosure, showing the nanowire mat formed over and between electrodes.
FIGS. 9b-9d are graphs showing the surface analytical characterization of the nanowire mats formed in accordance with the method of FIG. 7a and deposited on naked oxidized silicon substrates, performed using X-ray photoelectron spectroscopy taken in UHV conditions under the following sequence: (1) at room temperature; (2) at 200° C.; (3) at room temperature upon cooling down; (4) at 300° C.; and (5) at room temperature upon cooling down.
Figure 9C:
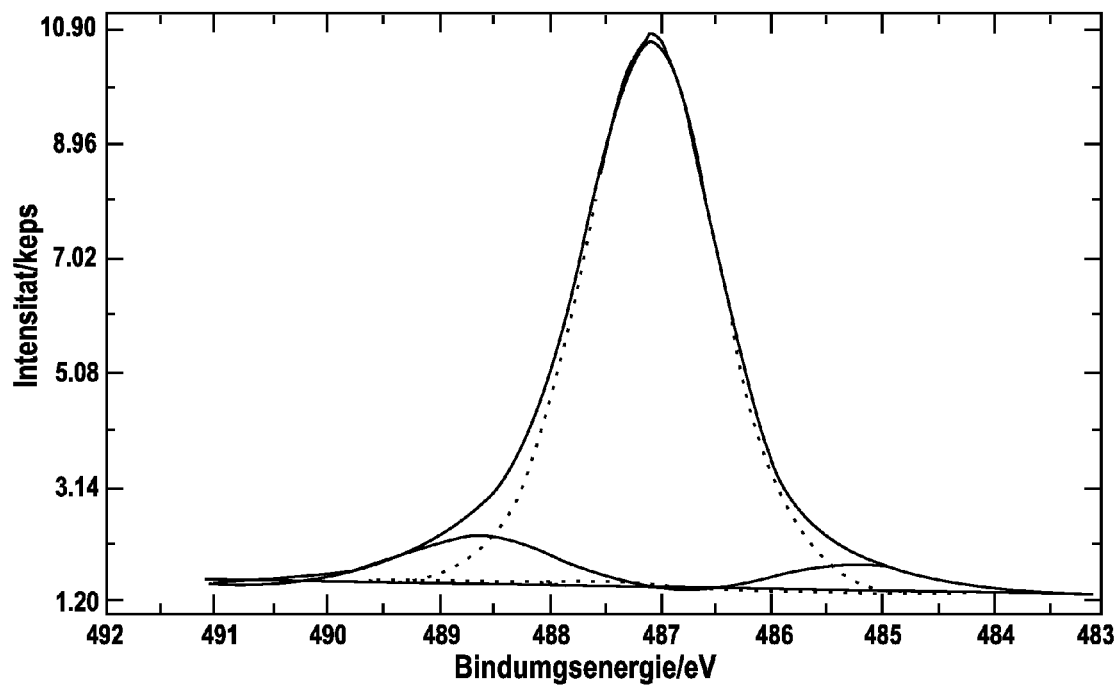
Figure 9D:
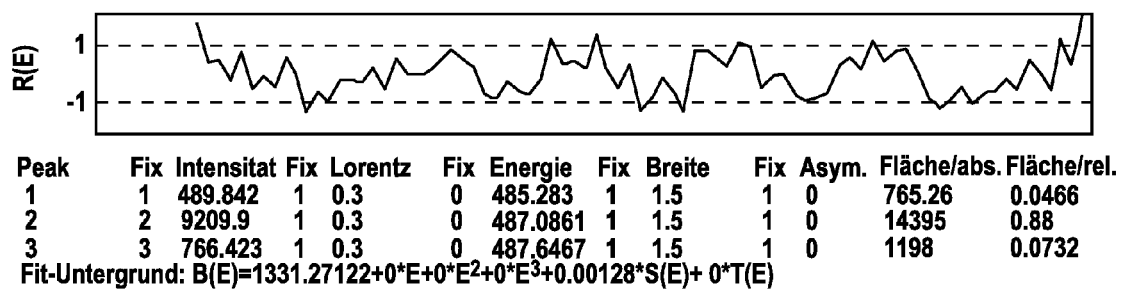

FIG. 8 shows the structural and chemical homogeneity of a $SnO_2$ nanowire mat. X-ray diffraction analysis confirmed that the $SnO_2$ nanowires are rutile single crystals with no other phases present. X-ray photoelectron spectroscopy spectra confirmed the generic purity of the $SnO_2$ nanowires and defined the degree of oxygen deficiency in the topmost surface layers of the nearly stoichiometric $SnO_2$ nanowires.

Surface analytical characterization of the $SnO_2$ nanowire mat samples deposited on pristine oxidized silicon substrates was performed in a temperature range of room temperature to 570 K using X-ray photoelectron spectroscopy (XPS). An ESCALAB 5 electron spectrometer was used (VG Scientific, East Grinstead, UK). The spectra of the nanowire mat were taken at a surface area of about 50 mm$^2$ by means of non-monochromatized $MgK_\alpha$ source. The XPS spectra were taken under UHV conditions under the following sequence: (1) at room temperature; (2) at 200° C., measured by a thermocouple attached to the substrate; (3) at room temperature again upon cooling down, which controlled by the thermocouple; (4) at 300° C.; and (5) at room temperature upon cooling down. The kinetic energies were measured using a 150° C. hemispherical energy analyzer. The binding energy scale was calibrated using a valve of 285 eC for the combination C is photopeak. The intensities of the photoelectron peaks were corrected for the individual cross sections (J. H. Scofield, *J. Electr. Spectr. Relat. Phenom.*, v. 8 (2), p. 129 (1976)) or using empirical atomic sensitivity factors (D. Briggs et al. (eds.), Practical Surface Analysis, v. 1, p. 635 (2d. 1983)). The as-deposited nanowires were found to be rather pure; the peak related to carbon contamination was small. Referring to Table 1, the near surface stoichiometry was determined by comparative analysis of the intensity and profile of the Sn 3d and O 1s lines.

TABLE 1

The [O]/[Sn] ratio in the $SnO_2$ nanowires estimated using XPS

| | Temperature | | | | |
|---|---|---|---|---|---|
| | Room | 200° C. | Room | 300° C. | Room |
| | → (direction of measurements) → | | | | |
| Sn 3d$_{5/2}$ intensity, un. | 14395 | 14850 | 14519 | 14367 | 14573 |
| O 1s intensity, un. | 4480 | 4399 | 4267 | 4167 | 4130 |
| [O]/[Sn] - corrected for individual cross sections | 1.60 | 1.52 | 1.51 | 1.49 | 1.45 |
| [O]/[Sn] - using empirical atomic sensitivity factors | 2.03 | 1.93 | 1.91 | 1.89 | 1.85 |

This data was consistent with other XPS studies of $SnO_2$ polycrystalline films and nanofibers. See Sinner-Hettenbach et al., *Surf Sci.* 47, 50-58 (2007); Moroseac et al., *Surf Sci.* 566, 1118-1123 (2004); and Wang et al., *J. Am. Ceram. Soc.* 88, 2059-2063 (2005). The data indicated an oxygen deficiency at the surface of the nanowires. Moreover, an approximately 8% decrease in the oxygen content occurred during annealing of the nanowires at 570 K in a vacuum This decrease can be attributed to thermally induced surface reduction. In air, these surface vacancies are repopulated, resulting in ionosorbed surface oxygen of the general form $o_{\beta S}^{-\alpha}$. The oxygen ionosoption leads to the depletion of n-type $SnO_2$ nanowires with electrons in 10 accordance to the surface reaction: $(\beta)/(2)O_2^{gas}+\alpha \cdot e^-+N_S \leftrightarrow O_{\beta S}^{-\alpha}$, where $\alpha\beta=\{1,2\}$ and accounts for the charge and molecular verses atomic nature of the chemisorbed oxygen, and $N_S$ is the concentration of the surface vacancies. Upon adsorbing a reducing gas X, the following surface reaction takes place with the ionosorbed oxygen: $\beta \cdot X^{gas}+O_{\beta S}^{-\alpha} \rightarrow +\beta \cdot XO^{gas}+\alpha \cdot e-$, resulting in donation of electrons back to the $SnO_2$ nanowire. FIG. 4b show the isothermal relative resistance change, $\Delta R/R=(R_{air}-R_{gas})/R_{air}$, of the nanowire mat averaged over the sensing elements as a function of the reducing gas concentration C. In accordance with previously reported results for compact metal oxide surfaces, the dependence of the isothermal relative resistance change on concentration obeyed the power law with an exponent equal to 0.61±0.06, 0.35±0.03, and 0.30±0.04 for CO, 2-propanol, and ethanol, respectively. This is consistent with Freundlich's adsorption isotherm.

Detection and Identification of a Target

The density, length, and number of nodes of the nanowire mats were shown to influence the resistance of the sensing elements. Sensing elements with larger densities of nanowires had lower resistance, while sensing elements with densities close to the percolation threshold had high resistance. The higher the density of the nanowire mats, the larger the contribution of the nodes to the signal response. The sensing elements can be tuned by adjusting the density of the nanowires within the sensing element, so that resistances of the sensing elements fit the dynamic range of the current preamplifiers of the electronic nose platform, such as a KAMINA platform, which has a dynamic range of current preamplifiers in a range of 0.01 to 100 MOhm.

Referring to FIG. 5, the performance of a multi-sensor having 38 sensing elements was tested under a temperature gradient for 2-propanol as the test gas. At approximately 600K, the sensing element reliably and reproducibly responded to as low as 500 ppb of 2-propanol in air.

Figure 10:
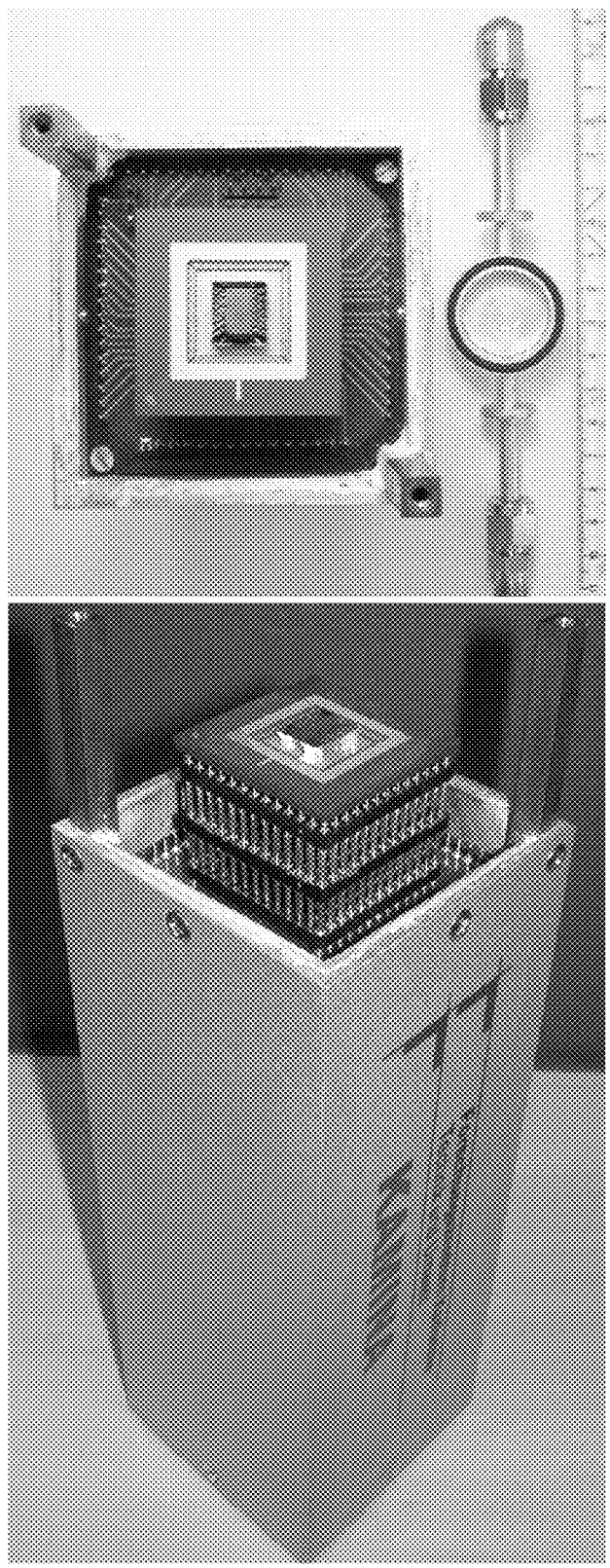
FIG. 10 is a photograph showing a KAMINA unit equipped with PGA-120 chip.
Figure 11:
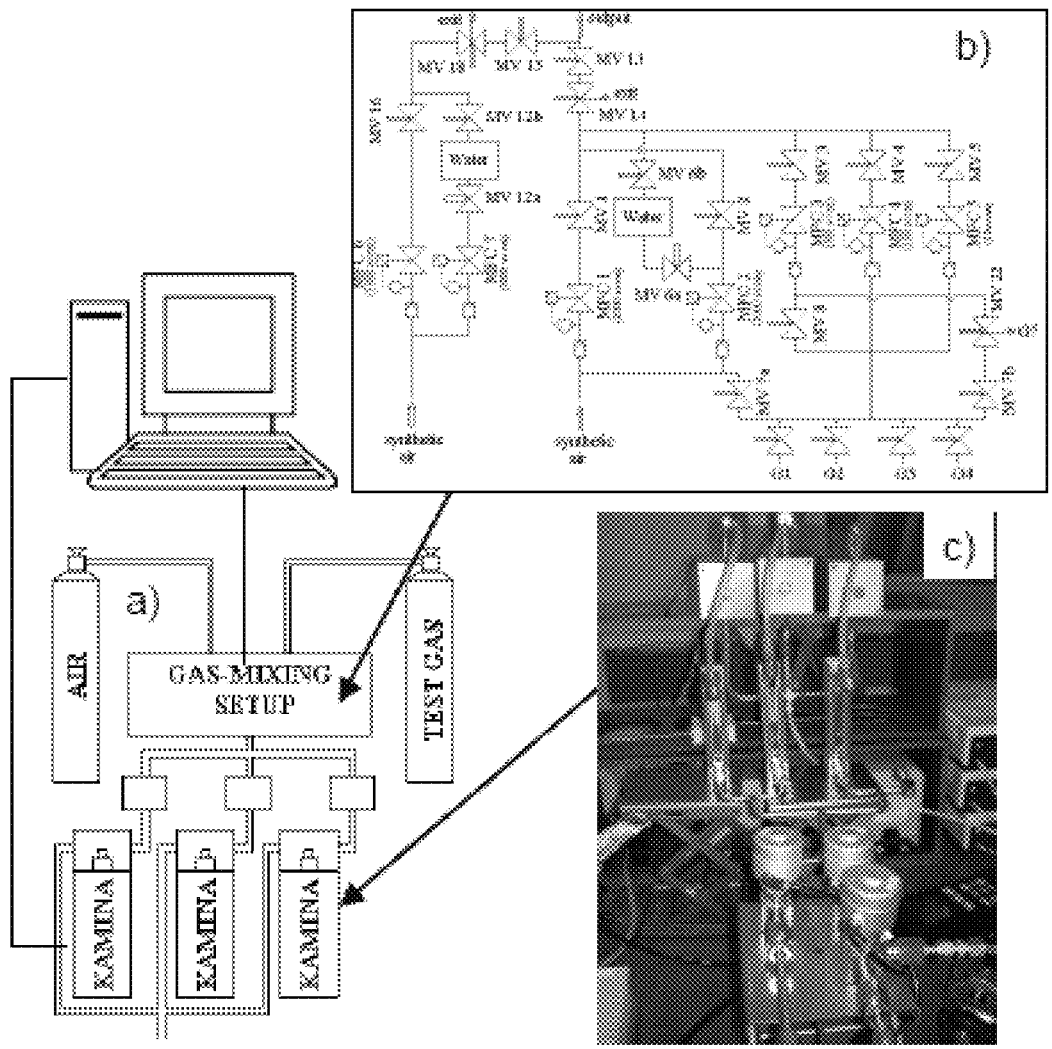

Referring to FIGS. 10 and 11, the multi-sensor was also tested using a gas mixture. The nanowire mats were placed in the KAMINA platform and exposed to three test gases at the gas mixing setup: (1) isopropanol, in a range of 0.5 ppm to 50 ppm; (2) ethanol, in a range of 0.5 ppm to 50 ppm; and (3) CO in a range of 0.5 ppm to 10 ppm. The entire gas flow rate was approximately 1.0 l/min, which was divided into 3 lines each with a rate of approximately 0.3 l/min per each KAMINA unit. The calibrated mixtures were ethanol at 510 ppm±2 rel. % in synthetic air; CO at 2030 ppm±2 rel. % in synthetic air; and isopropanol at 499.7 ppm±2 rel. % in $N_2$ (99.999% purity). The calibrated gas mixtures were further diluted with synthetic air (79% $N_2$, 21% $O_2$ mixture). The gas-mixing step was driven by PC through MKS controllers. The PC also contained MINOS software, which managed the operating conditions of each KAMINA unit. Test gas and clear air pulses were periodically alternated to sustain a test gas pulse of 30 min, at quasihomogenous temperature conditions, or a test gas pulse of 45 min at gradient temperature conditions, and a synthetic air pulse of 90 min Referring to FIG. 12, similar response data from all 38 sensing elements were collected, stored, and processed continuously by software to create images of the analyte in the conductivity patterns depending on the type of analyte and its concentration.

Linear Discriminant Analysis

A linear discriminate analysis was performed to test the discrimination power of the conductivity patterns quantitatively. This supervised multivarient pattern recognition method transfers the detectable responses, for example, resistances, into an optimized coordinate system of lower dimensionality equal to the number of test gases minus one.

Only quasistationary values of the resistance were taken into consideration for the analysis. The raw segment resistance data was processed as $$r_i \rightarrow \frac{R_i}{R_{med}},$$

wherein $R_i$ and $r_i$ are resistance and normalized resistance of the i-segment (i=[1,38]) in the microarray, respectively; $R_{med}$ is the median of all resistance data recorded during the measurements. The normalization is applied to eliminate the dependence of the multi-sensor resistance on the level of signal to a high extent. This can also enhance the stability of the recognition.

Referring to FIG. 6, as a result of the specificity of the detectable response (i.e. conductivity patterns in this example) to a specific gas, the multi-sensor response to one gas is distanced from that of another gas in the coordinate system. The more separated the conductivity patterns for the various test gases, the better the discrimination power of the multi-sensor. The gas discrimination power of the multi-sensor was estimated by a Mahalanobis distance in the LDA coordinate system. Since the LDA pattern recognition technique deals with estimation of the distribution of sensing element responses (i.e. resistances) over the multi-sensor rather than a sign change of the resistance upon exposure to the gas, LDA can be used not only for the data received under exposures of the multi-sensor to reducing analytes, but also to data recorded in air, with oxygen as the major active component.

The LDA demonstrated that the multi-sensor in accordance with an embodiment of the disclosure does not require the presence of a temperature gradient. The isothermal conductivity patterns of the multi-sensor were sufficient to obtain substantially different signal patterns for the various gases. The average Mahalanobis distance was about 15.3 for the isothermal testing condition. The variation of the density of nanowires in each sensing element provided sufficient distinctness to the individual sensing elements to allow for specificity of the gas response for the individual sensing elements. The discrimination power of the multi-sensor was enhanced when a temperature gradient was applied across the multi-sensor. On average, the Mahalanobis distance was about 34.2, more than double the distance between conductivity patterns as compared to the isothermal testing condition. Thus, the temperature gradient can enhance the identification of specific gases. For example, even chemically akin alcohols (ethanol and 2-propanol) were distinguished by their conductivity patterns.

The multi-sensor and method of detecting and identifying a target using the multi-sensor in accordance with various embodiment of the disclosure can achieve one or more benefits, including, for example, high gas permeability that does not drop with a reduction of nanowire diameter, as is the case with conventional nanostructured films. The dual response transduction mechanism of the nanowire mats, which is dependent upon a percolation regime, can allow for tuning of the sensitivity and discrimination power of the multi-sensor. Also, the single crystallinity of the nanowires can reduce and potentially eliminate the aging effects commonly experienced with conventional ultra-sensitive particulate thin films.

The invention has been described with reference to specific examples, which are intended to be illustrative only and not to be limiting of the invention. It will be apparent to those of ordinary skill in the art that changes, additions, and/or deletions may be made to the disclosed embodiments without departing from the spirit and scope of the invention.

What is claimed:

1. A multi-sensor for the detection and identification of an analyte and/or an irradiation, the multi-sensor comprising
    a substrate; and
    at least three sensing elements disposed on the substrate, each sensing element comprising
    two electrodes separated by a distance, and
    a nanowire mat disposed adjacent to and in contact with the electrodes, the nanowire mat comprising a plurality of nanowires defining a percolation network,
    wherein at least three such sensing elements are characterized by the density of the nanowires in the nanowire mat of each sensing element being different from each other.

2. The multi-sensor of claim 1, wherein the nanowires are selected from the group consisting of $SnO_2$ nanowires, $WO_3$ nanowires, $In_2O_3$ nanowires, $TiO_2$ nanowires, ZnO nanowires, NiO nanowires, CuO nanowires, $V_2O_5$ nanowires, $Ga_2O_3$ nanowires, and combinations thereof.

3. The multi-sensor of claim 1, wherein a surface of the nanowires is functionalized with a material selected from the group consisting of noble metals and oxides.

4. The multi-sensor of claim 1, comprising at least thirty-eight sensing elements.

5. The multi-sensor of claim 1, wherein the nanowires have a diameter in a range of about 20 nm to 500 nm.

6. The multi-sensor of claim 1, wherein the nanowires have a length in a range of about 1 μm to about 1000 μm.

7. The multi-sensor of claim 1, wherein the substrate is selected from the group consisting of a $SiO_2$/Si substrate, an $Al_2O_3$ substrate, a $Si_3N_2$ substrate, a Kapton film, a glass substrate, a sapphire substrate, a quartz substrate, and combinations thereof.

8. The multi-sensor of claim 1, wherein the electrode is formed of a material selected from the group consisting of platinum, gold, Cr, Ni, Ti, ITO, and combinations thereof.

9. The multi-sensor of claim 1, wherein the variation of the densities of the nanowires in the nanowire mats forms a density gradient across the multi-sensor.

10. The multi-sensor of claim 1, wherein the variation of the densities of the nanowires in the nanowire mats is random across the multi-sensor.

11. The multi-sensor of claim 1, wherein the distance between the electrodes of each sensing element is substantially equal for each sensing element.

12. The multi-sensor of claim 1, wherein the distance between electrodes of each sensing element is in a range of about 1 μm to about 200 μm.

13. The multi-sensor of claim 1, further comprising one or more heaters disposed on the substrate, wherein the heaters are capable of creating a temperature gradient across the multi-sensor.

14. A method of calibrating the multi-sensor of claim 1 for the detection and identification of an analyte and/or an irradiation, comprising:
    exposing the multi-sensor of claim 1 to a known analyte and/or a known irradiation;

detecting a change in resistance produced by each sensing element in response to the known analyte and/or known irradiation; and creating a response profile from the changes in resistance produced by the at least three sensing elements.

15. A method of detecting and identifying a target in a sample, the method comprising:

exposing the multi-sensor of claim 1 to a sample comprising or suspected of comprising a target; and detecting changes in resistance produced by each sensing element in response to exposure to the sample;

creating a response profile from the changes in resistance produced by the at least three sensing elements; and identifying the target by correlating at least a portion of the response profile to a known response profile.

16. The method of claim 15 further comprising creating the response profile using a pattern recognition method selected from the group consisting of principal component analysis, regression analysis, cluster analysis, linear-discriminant analysis, and combinations thereof.

17. The method of claim 15, further comprising applying a temperature gradient across the multi-sensor before exposing the sensor to the sample.

18. The method of claim 15, wherein the target is a gas.

19. The method of claim 15, wherein the target is a mixture of gases.

20. The method of claim 15, wherein the target is an irradiation.

21. The method of claim 20, wherein the irradiation is selected from the group consisting of UV radiation, thermal radiation, charged particle, radioactivity, and combinations thereof.

22. The method of claim 15, wherein the target is Ar ions.

* * * * *